United States Patent [19]

Seto et al.

[11] Patent Number: 5,534,225

[45] Date of Patent: Jul. 9, 1996

[54] CHEMICAL ANALYSIS ELEMENT SUPPLIER

[75] Inventors: Yoshihiro Seto; Yoshiyuki Doi, both of Kanagawa-ken, Japan

[73] Assignee: Fuji Photo Film Co., Ltd., Kanagawa, Japan

[21] Appl. No.: 498,467

[22] Filed: Jul. 5, 1995

[30] Foreign Application Priority Data

Jul. 5, 1994 [JP] Japan .................................... 6-153418

[51] Int. Cl.⁶ .................................................. G01N 37/00
[52] U.S. Cl. .............................. 422/64; 422/63; 422/104; 436/43; 436/46; 221/197
[58] Field of Search ................................. 422/63, 64, 65, 422/99, 104; 436/43, 46, 47, 48; 222/325; 221/211, 197, 14, 17

[56] References Cited

U.S. PATENT DOCUMENTS

| | | | |
|---|---|---|---|
| 3,992,158 | 11/1976 | Przybylowicz et al. | 23/253 |
| 4,053,381 | 10/1977 | Hamblem et al. | 204/195 M |
| 4,279,861 | 7/1981 | Jessop | 422/67 |
| 4,292,272 | 9/1981 | Kitajima et al. | 422/57 |
| 4,337,970 | 7/1982 | Gunderson | 285/136 |
| 4,477,575 | 10/1984 | Vogel et al. | 436/170 |
| 4,512,952 | 4/1985 | Blanding et al. | 422/63 |
| 4,855,109 | 8/1989 | Muraishi et al. | 422/63 |
| 5,019,347 | 5/1991 | Hiratsuka et al. | 422/56 |
| 5,030,418 | 7/1991 | Miyata | 422/63 |
| 5,043,143 | 8/1991 | Shaw et al. | 422/65 |
| 5,075,079 | 12/1991 | Kerr et al. | 422/64 |
| 5,089,419 | 2/1992 | Kuniyuki | 436/65 |
| 5,447,690 | 9/1995 | Sugaya | 422/64 |

FOREIGN PATENT DOCUMENTS

| | | |
|---|---|---|
| 0162302 | 11/1985 | European Pat. Off. . |
| 59-20858 | 2/1984 | Japan . |

*Primary Examiner*—Jill Warden
*Assistant Examiner*—Long V. Le
*Attorney, Agent, or Firm*—Sughrue, Mion, Zinn, Macpeak & Seas

[57] ABSTRACT

A chemical analysis element supplier has a cartridge container for storing a cartridge in which a plurality of chemical analysis elements are stored. The cartridge is inserted into the container through a cartridge insertion port which is formed in the top of the container. An element take-out mechanism takes out the chemical analysis element in the cartridge through an element take-out port which is formed in the bottom of the container. The element take-out mechanism is provided with a lifting member which is operative to move upward through the element take-out port to lift the cartridge in the container so that at least a part of the cartridge projects upward through the cartridge insertion port.

4 Claims, 5 Drawing Sheets

CHEMICAL ANALYSIS ELEMENT SUPPLIER

BACKGROUND OF THE INVENTION

1. Field of the Invention

This invention relates to a chemical analysis element supplier for supplying chemical analysis elements such as those for quantitatively analyzing the content of a specific chemical component contained in a sample liquid such as blood or urine or those for quantitatively analyzing the activity of particular ionic substances contained in a sample liquid such as blood or urine.

2. Description of the Related Art

There have been put into practice various "dry-to-the-touch" chemical analysis elements.

For example, there has been proposed, for instance, in U.S. Pat. Nos. 3,992,158; 4,292,272 and 5,019,347 and European Patent 0 162 302B and put into practice a "dry-to-the-touch" chemical analysis film with which the content of a specific chemical component contained in a sample liquid, the activity thereof or the content of a solid component can be quantitatively analyzed by only spotting a droplet of the sample liquid on the film. As such a dry chemical analysis film, there has been known an integrated multi-layered chemical analysis film (sometimes referred to as "multi-layered chemical analysis element") comprising a support sheet of organic polymer and a reagent layer formed on the support sheet. The reagent layer contains therein a reagent whose optical density changes by chemical reaction, biochemical reaction, immunoreaction or the like with a specific biochemical component contained in the sample liquid. A spreading layer is sometimes formed over the reagent layer. Further a dry chemical analysis film which is formed of filter paper and has one or more layers has been proposed, for instance, in U.S. Pat. No. 4,477,575, and partly put into practice.

The chemical analysis film is generally in the form of a film chip of a predetermined shape such as square or rectangle. In the past, the film chip is generally provided with a frame of organic polymer or the like for facilitating automated handling of the film chip. The film chip provided with such a frame is generally called a chemical analysis slide. However in a chemical analysis apparatus we have previously proposed, the chemical analysis film chip is used as it is without frame. The chemical analysis film without frame is generally referred to as "a frameless chemical analysis film".

When quantitatively analyzing the chemical components or the like contained in a sample liquid using such a chemical analysis film (a chemical analysis slide or a frameless chemical analysis film), a droplet of the sample liquid is spotted on the chemical analysis film (on the spreading layer when the film is provided with a spreading layer and directly on the reagent layer when the film is provided with no spreading layer) and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the film is projected onto the film and the optical density of the film is measured. Then the concentration or the activity of the component to be analyzed is determined on the basis of the optical density using a calibration curve (standard curve) which represents the relation between the concentration of the biochemical component and the optical density.

Further there has been proposed, for instance, in U.S. Pat. Nos. 4,053,381 and 4,437,970 and put into practice a "dry-to-the-touch" electrolyte analysis slide for quantitatively analyzing the activity of particular ionic substances contained in a sample liquid such as blood or urine in a potentiometric way. The electrolyte analysis slide is a kind of electrochemical sensors and comprises an ion selective electrode.

In this specification, the term "chemical analysis element" should be broadly interpreted to include the chemical analysis slide, the frameless chemical analysis film, the single-layered or multi-layered chemical analysis film formed of filter paper (with or without frame), and the electrolyte analysis slide described above.

A plurality of chemical analysis elements are stacked in a cartridge and a plurality of cartridges containing therein different types of chemical analysis elements (chemical analysis elements for different components to be analyzed) are loaded in a chemical analysis element supplier. According to the kind of analyte (the component to be analyzed), a chemical analysis element is taken out from one of the cartridges and is supplied to a chemical analysis apparatus. For example, in a chemical analysis element supplier disclosed in Japanese Unexamined Patent Publication No. 59(1984)-20858 and U.S. Pat. Nos. 4,512,952 and 5,089,418, a plurality of cartridges are arranged in a circle on a support and the support is rotated to bring a selected cartridge to an element take-out position. In the element take-out position, a slide member which slides from the inside out pushes out the chemical analysis elements in the cartridge one by one.

As a mechanism for removing the cartridge after use from the supplier, one having a dropping mechanism which automatically drops the cartridge or one having a mechanism which opens a lid or a shutter of the supplier to give the operator access to the cartridge inside the supplier may be used.

However the former mechanism is disadvantageous in that a dropping mechanism and a space for dropping the cartridge are required below the supplier, which disturbs miniaturization of the apparatus and adds to the cost.

That is, an element take-out mechanism for taking out the chemical analysis element from the cartridge and a shutter opening mechanism for opening and closing an element take-out opening of the supplier and the like are disposed below the supplier and accordingly it is difficult to dispose the dropping mechanism below the supplier without interference with those mechanisms.

The latter mechanism is disadvantageous in that it is difficult to ensure storing performance of the supplier. That is, in order to stabilize humidity in the supplier, it is preferred that the cartridge inlet opening and the film take-out opening be as small as possible, and in order to store the chemical analysis elements at a low temperature, it is preferred that the wall of the supplier be as thick as possible, which results in a small and deep cartridge inlet opening and makes it difficult to take out the cartridge through the cartridge inlet opening.

SUMMARY OF THE INVENTION

In view of the foregoing observations and description, the primary object of the present invention is to provide a chemical analysis element supplier in which the chemical analysis element cartridges can be easily taken out without adversely affecting storing performance of the supplier.

The chemical analysis element supplier of the present invention comprises a cartridge container for storing a cartridge in which a plurality of chemical analysis elements are stored and an element take-out means moves up and down and which takes out the chemical analysis element in the cartridge. The container has a cartridge insertion port which is formed in the top of the container and through which the cartridge is inserted into the container and an element take-out port which is formed in the bottom of the container to gives access to the cartridge in the container. The element take-out means moves up and down and takes out the chemical analysis element in the cartridge through the element take-out port. The chemical analysis element supplier of the present invention is characterized in that the element take-out means is provided with a lifting member which is operative to move upward through the element take-out port to lift the cartridge in the container so that at least a part of the cartridge projects upward through the cartridge insertion port.

In a preferred embodiment of the present invention, the element take-out means is provided with a positioning arm which locates the cartridge with respect to the element take-out means when the element take-out means takes out the chemical analysis element from the cartridge and the lifting member is the positioning arm.

In another preferred embodiment of the present invention, the element take-out means is provided with a suction pad which holds the chemical analysis element under a suction force and takes out the chemical analysis element from the cartridge, and the lifting member is the suction pad.

In the chemical analysis element supplier of this invention, when the cartridge is to be taken out from the container, the lifting member is moved upward through the element take-out port to lift the cartridge in the container so that at least a part of the cartridge projects upward through the cartridge insertion port. Accordingly, the operator can easily hold the cartridge without inserting his fingers into the container and the container can be formed without taking into facility of taking out the cartridge. Thus the moisture-proofness and heat retaining properties of the container can be easily ensured without adding to the cost and/or the size of the supplier.

Further when the member such as the positioning arm or the suction pad which is inherent to the element take-out means doubles as the lifting member, no additional lifting member is required and the mechanism of the supplier can be further simplified.

DESCRIPTION OF THE PREFERRED EMBODIMENT

Figure 1:
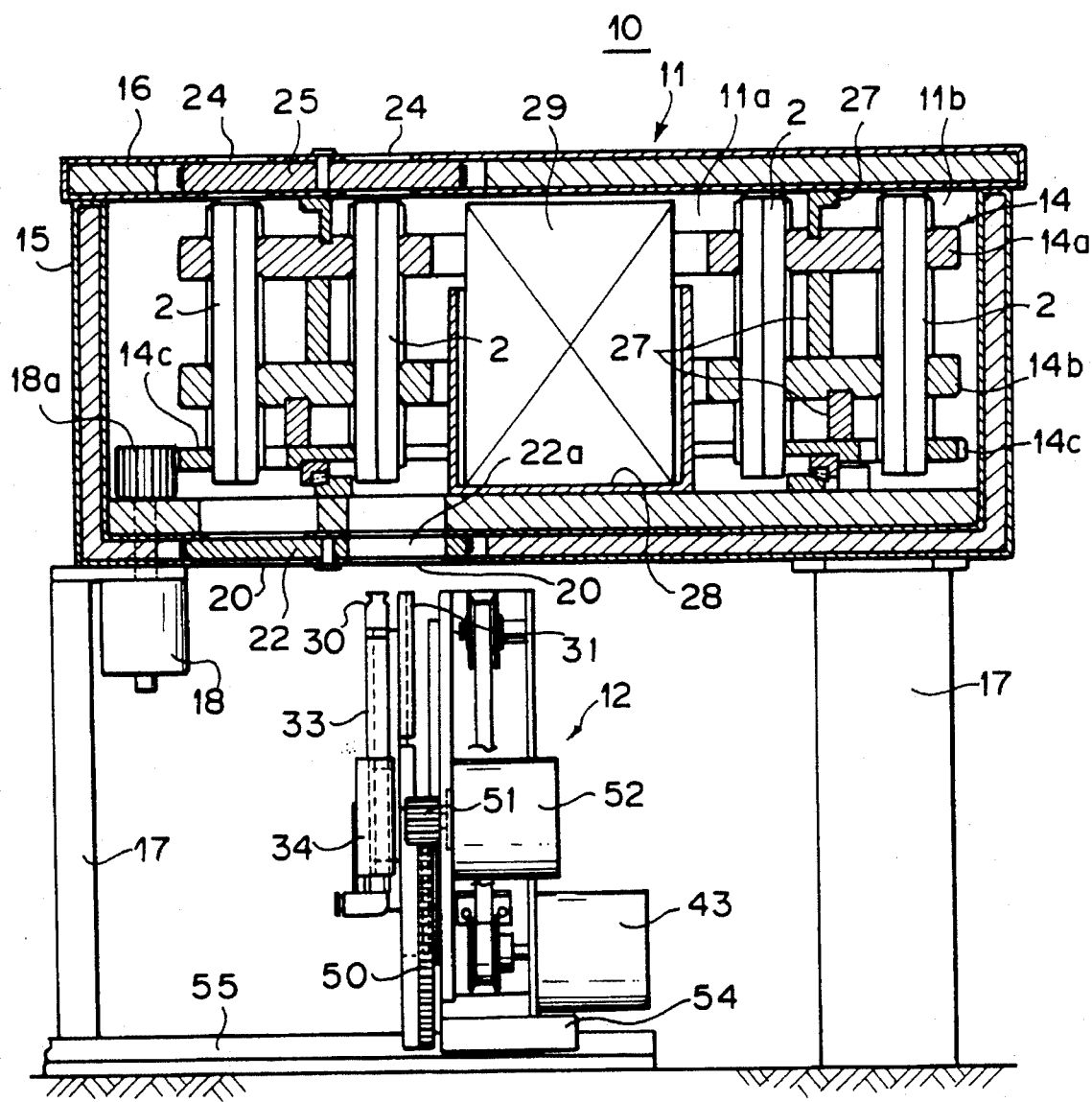
FIG. 1 is a cross-sectional view showing a chemical analysis element supplier in accordance with an embodiment of the present invention.
Figure 2:
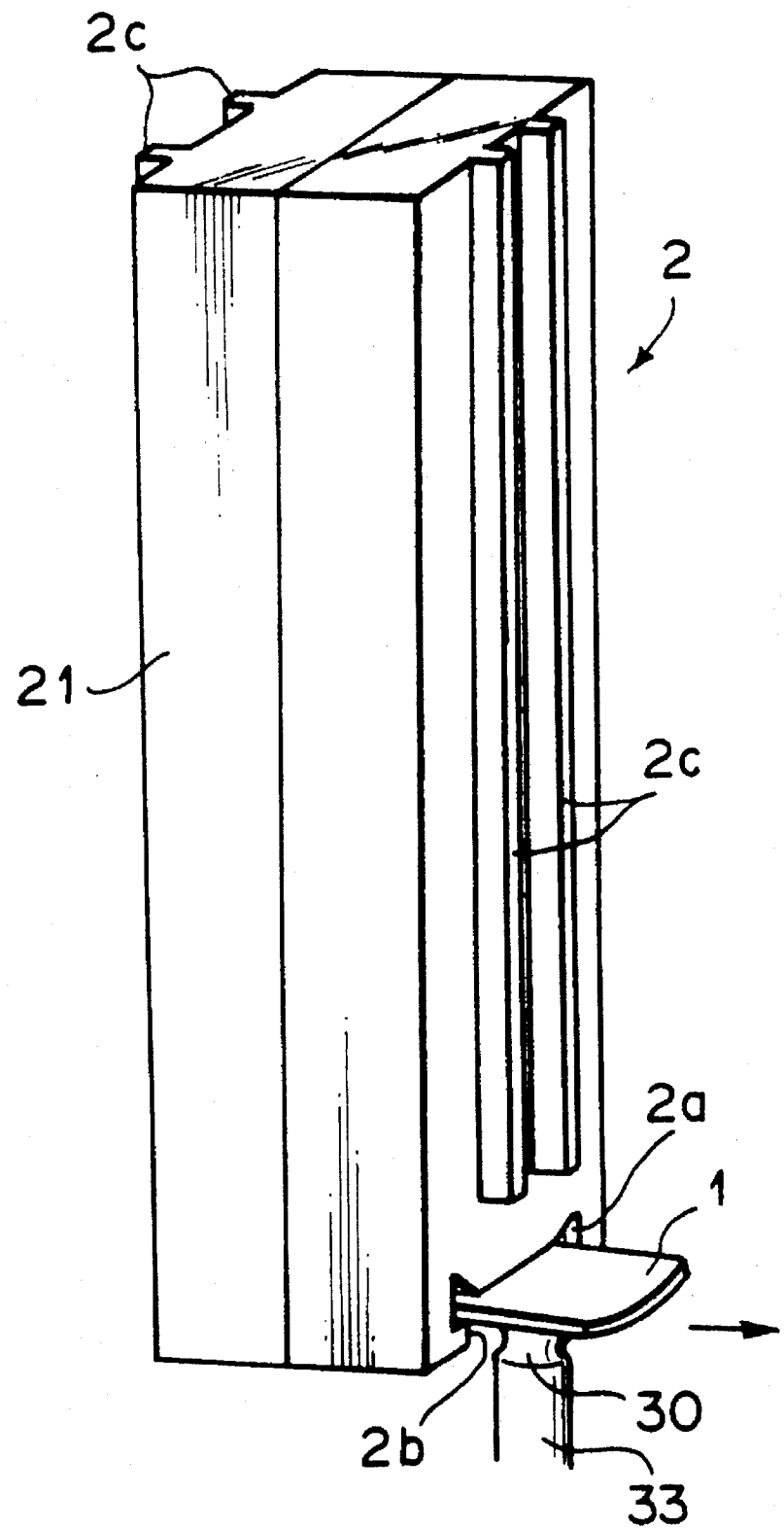
FIG. 2 is a perspective view for illustrating the manner of taking out a chemical analysis film from a cartridge.

In FIG. 1, a chemical analysis element supplier 10 in accordance with an embodiment of the present invention is for use in a biochemical analysis apparatus and is provided with a container 11 for storing therein a plurality of chemical analysis element cartridges 2. In each of the cartridges 2, a plurality of virgin frameless chemical analysis films 1 are stacked. Each chemical analysis film 1 is substantially rectangular or square in shape as shown in FIG. 2. The chemical analysis element supplier 10 is further provided with a film take-out means 12 for taking out the chemical analysis films 1 one by one from the cartridges 2 in the container 11.

In this particular embodiment, the frameless chemical analysis film 1 comprises a light-transmissive support sheet formed of a plastic sheet such as polyethylene terephthalate, polystyrene or the like, a reagent layer and a spreading layer. That is, the frameless chemical analysis film 1 is formed by coating or bonding the reagent layer on the support sheet and laminating the spreading layer on the reagent layer. The chemical analysis film 1 is not provided with any frame.

The reagent layer comprises at least one layer composed of a porous layer or a hydrophilic polymer binder such as gelatin containing therein a detecting reagent component which selectively reacts with an analyte and a reagent component (chemical analysis reagent, immunoassay reagent or the like) which is necessary for coloring reaction. The spreading layer is formed of a material resistant to rubbing such as woven or knitted fabric (or cloth) of synthetic fiber such as polyester or of blend of natural fiber and synthetic fiber, or paper and functions as a protective layer. Further the spreading layer causes sample liquid applied thereto to uniformly spread over the reagent layer.

The chemical analysis films 1 are stored in the cartridges 2 for the respective analytes.

As shown in FIG. 2, the cartridge 2 comprises a box-like cartridge body 21 in which a plurality of chemical analysis films 1 are stored in a stack. The cartridge body 21 is a rectangular column in shape and is formed by mating together left and right halves. A first opening 2a is formed in one side wall of the cartridge body 21 near the bottom thereof. The first opening 2a is in the form of a slit open in said one side wall and has such a width that one chemical analysis film 1 can pass therethrough. A U-shaped second opening 2b through which a take-out suction cup 30 for taking out the film 1 enters the cartridge body 21 is formed in the bottom of the cartridge body 21. Though not shown, a limiting member for urging the stack of the chemical analysis films 1 toward the second opening 2b is provided in the cartridge body 21.

A pair of outer ribs 2c are formed on each of the left and right side walls of the cartridge body 21. The space between the outer ribs 2c on the left side wall differs from that on the right side wall to prevent insertion of the cartridge 2 into a cartridge holding portion in a support 14 of the container 11 in a wrong position. Further the outer ribs 2c hold the cartridge 2 in the cartridge holding portion.

The support 14 is like a disk and is provided with a plurality of cartridge holding portions which are arranged in inner and outer circles.

As shown in FIG. 1, the container 11 comprises a container body 15 which has a bottom wall and a peripheral wall and opens upward and a lid 16 which closes the container body 15. The support 14 is supported for rotation on the bottom of the container body 15. Each of the container body 15 and the lid 16 comprises inner and outer plate materials and heat insulating material sandwiched between the inner and outer plate materials. The container 11 is supported above a base by a frame 17 and the film take-out means 12 is disposed below the container 11.

The support 14 comprises upper, intermediate and lower disk members 14a, 14b and 14c and gear teeth are formed on the peripheral surface of the lower disk member 14c. A drive gear 18a fixed to an output shaft of a support drive motor 18a is in mesh with the gear teeth on the lower disk member 14c. The lower ends of the ribs 2c on one side of the cartridge 2 rest on the lower disk member 14c and hold the cartridge 2 in the support 14.

Figure 5:
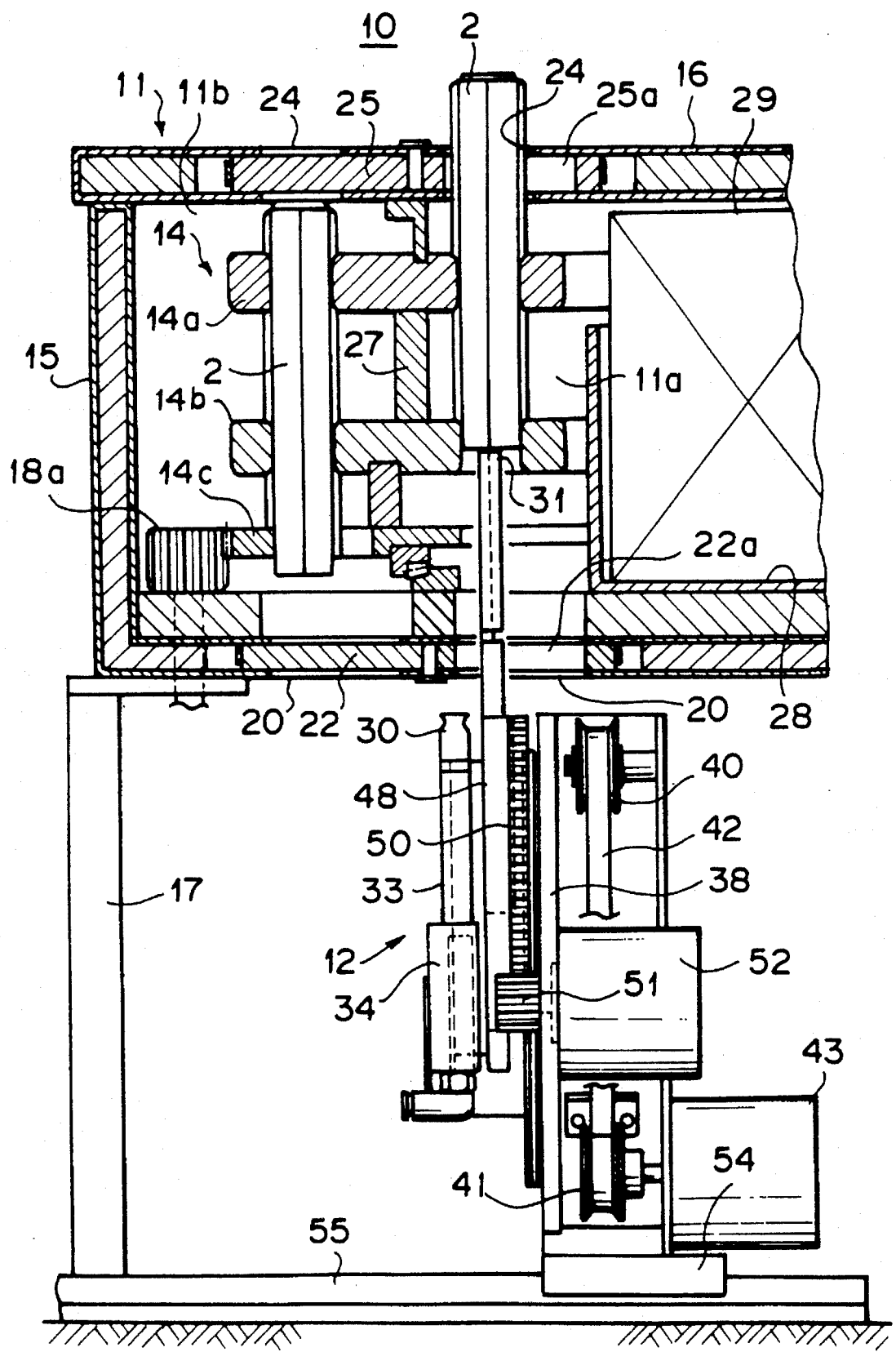
FIG. 5 is a fragmentary cross-sectional view for illustrating the manner of taking out the cartridge from the container.

As clearly shown in FIG. 5, inner and outer film take-ports 20 are formed in the bottom wall of the container body 15 at a portion opposed to a film take-out position of the film take-out means 12 and a disk-like lower shutter 22 selectively opens one of the inner and outer film take-out ports 20. Further inner and outer cartridge insertion ports 24 are formed in the lid 16 respectively in alignment with the inner and outer film take-out ports 20, and a disk-like upper shutter 25 selectively opens one of the inner and outer cartridge insertion ports 24.

The heat insulating material near the inner and outer film take-out ports 20 is removed and the lower shutter 22 is mounted between the inner and outer plate members of the bottom wall of the container body 11 for rotation about an axis disposed between the inner and outer film take-out ports 20. An opening 22a is formed in the lower shutter 22 and the lower shutter 22 is rotated by an electric motor (not shown) by way of a drive belt (not shown) among a position where the opening 22a is in alignment with the inner film take-out port 20, a position where the opening 22a is in alignment with the outer film take-out port 20, and a position where the opening 22a is in alignment with neither the inner film take-out port 20 nor the outer film take-out port 20.

Similarly the heat insulating material near the inner and outer cartridge insertion ports 24 is removed and the upper shutter 25 is mounted between the inner and outer plate members of the lid 16 for rotation about an axis disposed between the inner and outer cartridge insertion ports 24. An opening 25a is formed in the upper shutter 25 and the upper shutter 25 is rotated by an electric motor (not shown) by way of a drive belt (not shown) among a position where the opening 25a is in alignment with the inner cartridge insertion port 24, a position where the opening 25a is in alignment with the outer cartridge insertion port 24, and a position where the opening 25a is in alignment with neither the inner film cartridge insertion port 24 nor the outer cartridge insertion port 24.

A partition member 27 (FIG. 1) is provided in the support 14 between the inner cartridge holding portions (arranged in the inner circle) and the outer cartridge holding portions (arranged in the outer circle) and divides the inner space of the container 11 into inner and outer chambers 11a and 11b. An inner dehumidifying agent holding portion 28 is formed in the inner chamber 11a at the center thereof, and a dehumidifying agent (humidity control agent) 29 is contained in the inner dehumidifying agent holding portion 28. An outer dehumidifying agent holding portion (not shown) is formed in a part of the peripheral wall of the outer chamber 11b and a different dehumidifying agent is contained in the outer dehumidifying agent holding portion. Thus, the inner and outer chambers 11a and 11b are kept under different humidity conditions and cartridges 2 storing therein chemical analysis films 1 to be stored under the humidity condition in the inner chamber 11a are loaded in the inner chamber 11a while cartridges 2 storing therein chemical analysis films 1 to be stored under the humidity condition in the outer chamber 11b are loaded in the outer chamber 11b.

Figure 3:
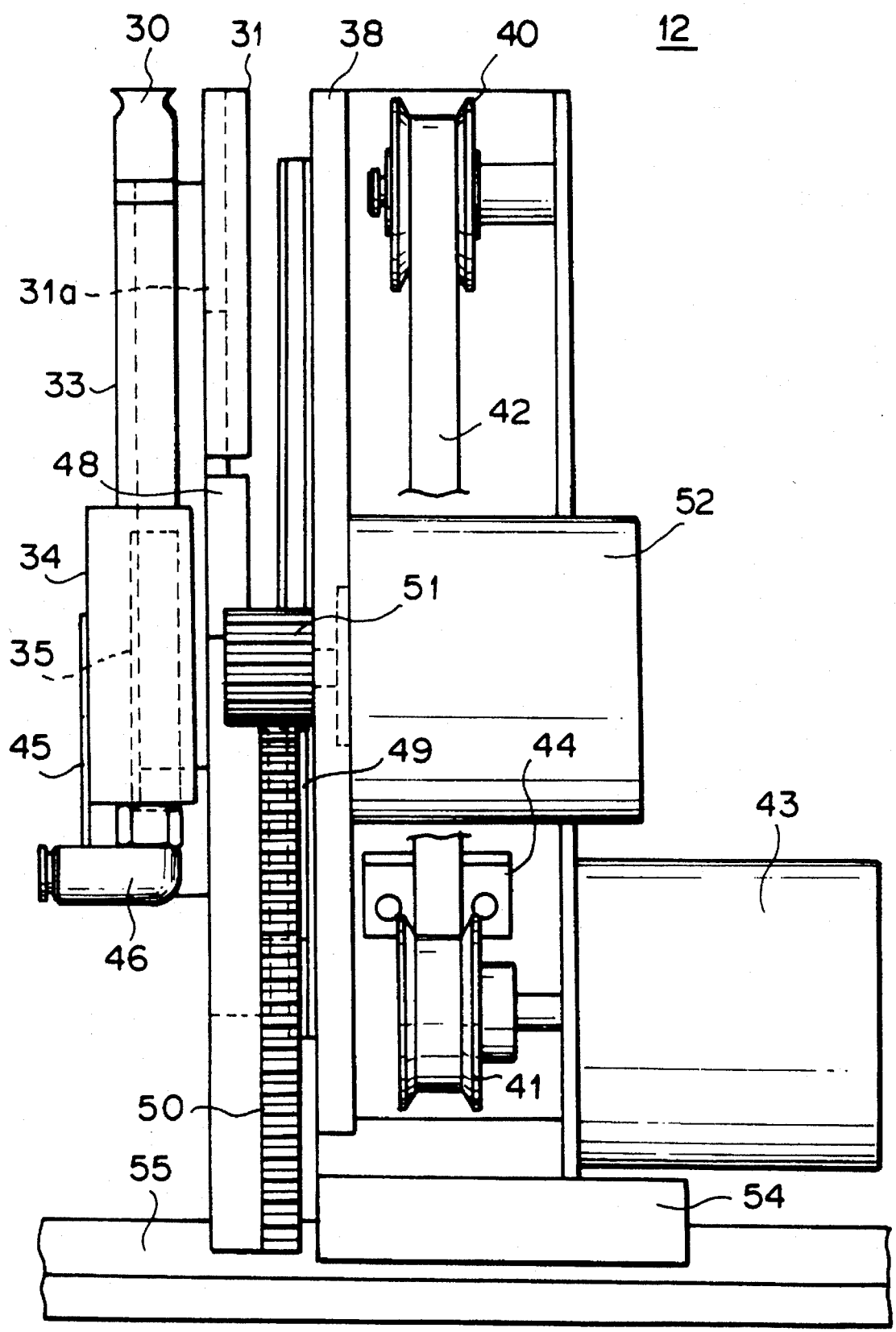
FIG. 3 is a schematic front view showing the film take-out means.
Figure 4:
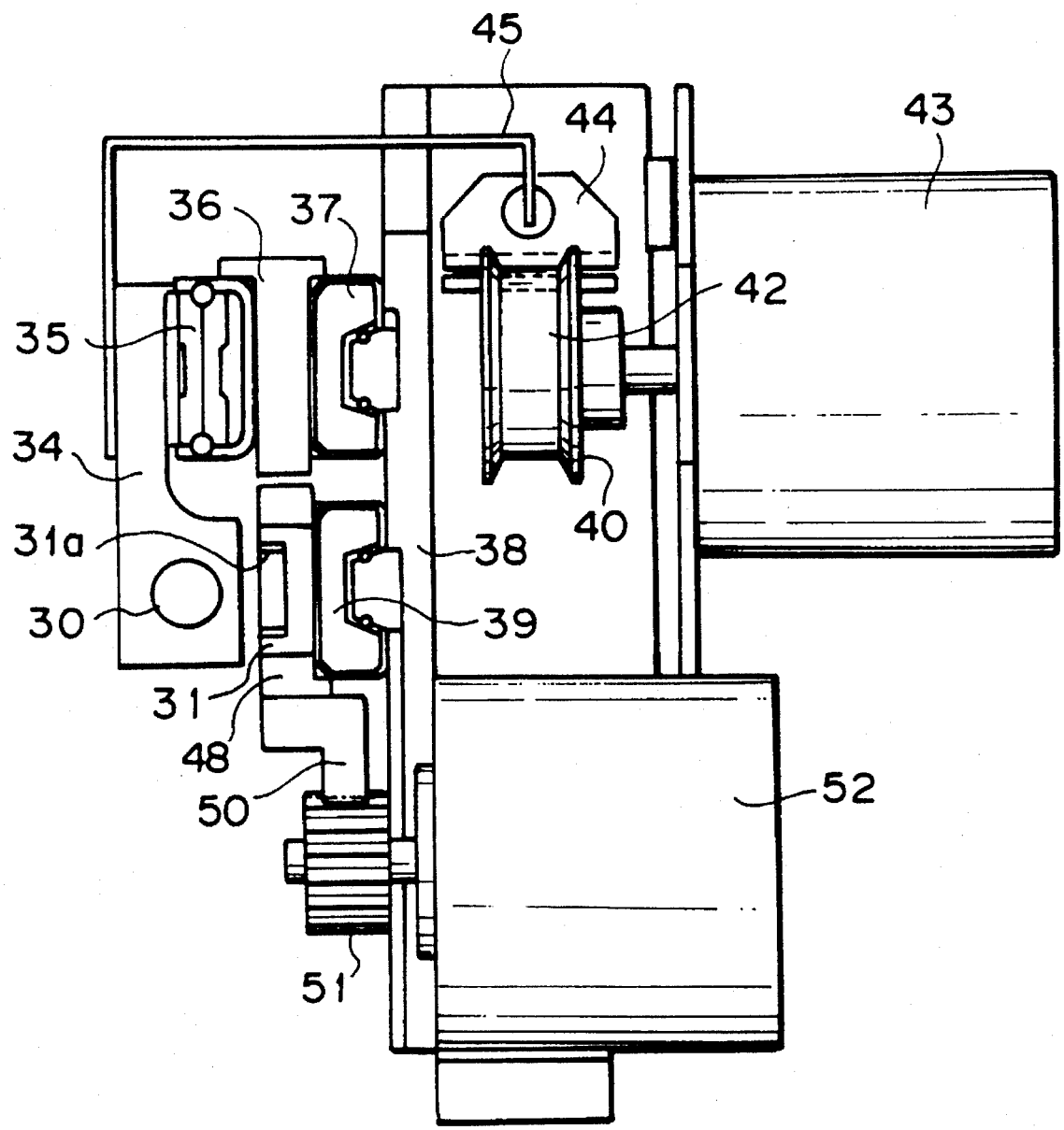
FIG. 4 is a schematic plan view of the film take-out means.

As shown in FIGS. 3 and 4, the film take-out means 12 comprises a take-out suction pad 30 which holds the chemical analysis film 1 under a suction force and a positioning arm 31 which positions the cartridge 2. The suction pad 30 and the positioning arm 31 are supported for up and down movement, respectively.

The suction pad 30 is supported on the upper end of a tubular shaft member 33 which is fixed to a suction pad holder 34 at its lower end. The suction pad holder 34 is supported on an intermediate member 36 by way of a first slider 35 to be movable up and down. The intermediate member 36 is supported on a vertical base member 38 by way of a second slider 37 to be movable up and down. Upper and lower pulleys 40 and 41 are disposed adjacent to the base member 38 and a drive belt 42 is passed around the pulleys 40 and 41. The lower pulley 41 is driven by a suction pad drive motor 43. One end of a connecting plate 45 is connected to the belt 42 by a fastener 44 and the other end of the connecting plate 45 is connected to the suction pad holder 34.

With this arrangement, when the belt 42 is driven by the motor 43, the suction pad holder 34 and the suction pad 30 are moved up or down by way of the connecting plate 45 in two steps by virtue of the first and second sliders 35 and 37. A suction pipe 46 is connected to the suction pad holder 34.

The positioning arm 31 which is disposed adjacent to the suction pad 30 is fixed to an arm holder 48 at the lower end portion thereof. A recess 31a adapted to slide on the outer ribs 2c of the cartridge 2 is formed on one side of the upper end portion of the positioning arm 31. The arm holder 48 is supported on the base member 38 by way of a third slider 49 to be movable up and down relative to the base member 38. A rack 50 is provided on one side of the arm holder 48 and is in mesh with a pinion 51 fixed to a drive shaft of an arm motor 52 mounted on the base member 38.

With this arrangement, when the pinion 51 is driven by the arm motor 52, the arm holder 48 and the positioning arm 31 are moved up or down by way of the rack 50. As will be described later, the arm 31 is moved upward to lift the cartridge 2 to a position where the upper portion of the cartridge 2 projects upward through the cartridge insertion port 24.

The base member 38 has a block member 54 on its lower end and the block member 54 is engaged with a rail 55 to be slidable along the rail 55 in a radial direction of the support 14. A drive mechanism (not shown) moves the block member 54 along the rail 55, thereby positioning the film take-out means 12.

The operation of the chemical analysis element supplier 10 will be described, hereinbelow. Assuming that all the cartridge holding portions of the container 11 are loaded with the cartridges 2 as shown in FIG. 1, when a chemical analysis film 1 stored in one of the cartridges 2, the support motor 18 is driven to bring the cartridge 2 to the film-take-out position.

The lower shutter 22 is rotated to bring the opening 22a into alignment with the inner film take-out port 20 (assuming that the cartridge 2 is in one of the inner cartridge holding portions) with the cartridge insertion ports 24 closed by the upper shutter 25. Then the film take-out means 12 is moved to a position where the suction pad 30 is positioned just below the center of the cartridge 2. Then the positioning arm 31 is moved upward through the film take-out port 20 so that the lower end portions of the outer ribs 2c are received in the recess 31a, thereby locating the cartridge 2 relative to the suction pad 30.

Thereafter the suction pad 30 is moved upward through the film take-out port 20 into the second opening 2b of the cartridge 2 and is pressed against the lowermost chemical analysis film 1 in the cartridge 2, whereby the suction pad 30 holds the lowermost chemical analysis film 1 under a suction force. While holding the film 1, the suction pad 30 is slightly moved downward so that opposite edge portions of the film 1 abut against the edges of the second opening 2b and the film 1 is curled upward and then the suction pad 30 is slid radially inward of the support 14 along the second opening 2b through the first opening 2a to bring the film 1 outside the cartridge 2 as shown in FIG. 2. Thereafter the suction pad 30 with the film 1 is moved downward through the film take-out port 20. Thus the film 1 is taken out from the supplier 10.

Even if the upward movements of the positioning arm 31 and the suction pad 30 urges upward the cartridge 2, the cartridge 2 is prevented from moving upward by abutment of the top of the cartridge 2 against the lower surface of the upper shutter 25 which is closed at this time.

When the cartridge 2 is to be taken out from the container 11, for instance, after all the films 1 in the cartridge 2 have been taken out, the upper and lower shutters 25 and 22 are rotated to open the corresponding cartridge insertion port 24 and the film take-out port 20. Then the film take-out means 12 is moved to a position where the positioning arm 31 is positioned just below the center of the cartridge 2 and the positioning arm 31 is moved upward so that the upper end of the arm 31 is brought into abutment against the bottom of the cartridge 2 and pushes upward the cartridge 2. When the upper end portion of the cartridge 2 comes to project upward through the cartridge insertion port 24 by a predetermined length, the positioning arm 31 is stopped and the cartridge 2 is taken out by the operator and then another cartridge 2 is inserted through the insertion port 24.

Though, in the embodiment described above, the cartridge 2 is pushed upward by the positioning arm 31, the cartridge 2 may be pushed upward by the suction pad 30. Further the cartridge 2 may be pushed upward by an additional lifting means.

Further though, in the embodiment described above, a plurality of cartridges 2 are loaded in the container 11 in two circles, the present invention may be applied to a container in which only one cartridge 2 is loaded or a container in which a plurality of cartridges 2 are loaded in a single circle or in three or more circles.

As can be understood from the description above, in accordance with the present invention, the cartridges 2 in the container can be easily taken out without adversely affecting the storing performance of the container and without adding to the cost. Further, the mechanism is not complicated and the size of the supplier is not increased.

What is claimed is:

1. A chemical analysis element supplier comprising a cartridge container for storing a cartridge in which a plurality of chemical analysis elements are stored, the container having a top, a bottom, a cartridge insertion port, which is formed in the top of the container and through which the cartridge is inserted into the container, and an element take-out port which is formed in the bottom of the container to give access to the cartridge in the container; and an element take-out means which moves up and down and takes out a selected one of the chemical analysis elements in the cartridge through the element take-out port, wherein said element take-out means is provided with a lifting member which is operative to move upward through the element take-out port to abut and lift the cartridge in the container so that at least a part of the cartridge projects upward through the cartridge insertion port so as to be exposed outside of the container, thereby to permit the cartridge to be removed and replaced with another cartridge.

2. The chemical analysis element supplier as defined in claim 1, in which said cartridge insertion port is provided with a shutter which selectively opens and closes the cartridge insertion port and said lifting member lifts the cartridge with the cartridge insertion port opened.

3. The chemical analysis element supplier as defined in claim 1, in which said element take-out means is provided with a positioning arm which locates the cartridge with respect to the element take-out means when the element take-out means takes out the selected chemical analysis element from the cartridge and said lifting member serves as the positioning arm.

4. The chemical analysis element supplier as defined in claim 1, in which said element take-out means is provided with a suction pad which holds the selected chemical analysis element under a suction force and takes out the selected chemical analysis element from the cartridge, and said lifting member includes the suction pad.

* * * * *